United States Patent [19]
Rassaerts et al.

[11] 3,949,009
[45] Apr. 6, 1976

[54] PROCESS FOR PREPARING TRICHLOROETHYLENE

[75] Inventors: Heinz Rassaerts, Hallenin-Rif, Sbg, Austria; Gerhard Sticken, Lippramsdorf; Wilhelm Knepper, Marl, both of Germany

[73] Assignee: Chemische Werke Huls Aktiengesellschaft, Germany

[22] Filed: Mar. 26, 1974

[21] Appl. No.: 454,786

[30] Foreign Application Priority Data
Apr. 4, 1973 Germany............................ 2316723

[52] U.S. Cl....... 260/654 H; 260/654 D; 260/658 R
[51] Int. Cl.²........................................ C07C 21/10
[58] Field of Search..................... 260/658 R, 654 H

[56] References Cited
UNITED STATES PATENTS

| | | | |
|---|---|---|---|
| 2,547,139 | 4/1951 | Randall............................ | 260/654 H |
| 3,344,197 | 9/1967 | Reiche et al..................... | 260/658 R |
| 3,535,394 | 10/1970 | Pregaglia et al. ............... | 260/658 R |
| 3,637,875 | 1/1972 | Correia et al.................... | 260/658 R |

*Primary Examiner*—Delbert E. Gantz
*Assistant Examiner*—Joseph A. Boska
*Attorney, Agent, or Firm*—Gilbert L. Wells

[57] ABSTRACT

A process for preparing trichloroethylene by chlorinating 1,2-dichloroethane in the liquid phase in the presence of ethylene followed by pyrolytic chlorination or dehydrochlorination of the reaction product. The 1,2-dichloroethane is chlorinated in the liquid phase in a bubble column reactor in the presence of 1 – 10 mole percent of ethylene with a chlorine/1.2-dichloroethane feed ratio of about 0.7 – 1.4/1, a temperature of about 40° to 150°C with superficial velocities exceeding 8 cm/sec. and gas dwell times of about 0.3 to 10 seconds. The chlorinated product is reacted in the gas phase with recirculated tetrachloroethanes and about 20 – 70 moles of chlorine per 100 moles of chlorinated hydrocarbons at temperatures of about 380° to 500°C and dwell times of about 20 to 30 seconds. This gas phase reaction product is separated by distillation into a low-boiling fraction containing predominantly dichloroethylenes and a high boiling fraction containing predominantly trichloroethylene. The low boiling fraction is reacted in the liquid phase with equimolar amounts of chlorine at temperatures of about 60° – 150°C to obtain the tetrachloroethanes that are recirculated. The high boiling fraction is then separated by distillation into the trichloroethylene product and higher boiling point side products.

11 Claims, 1 Drawing Figure

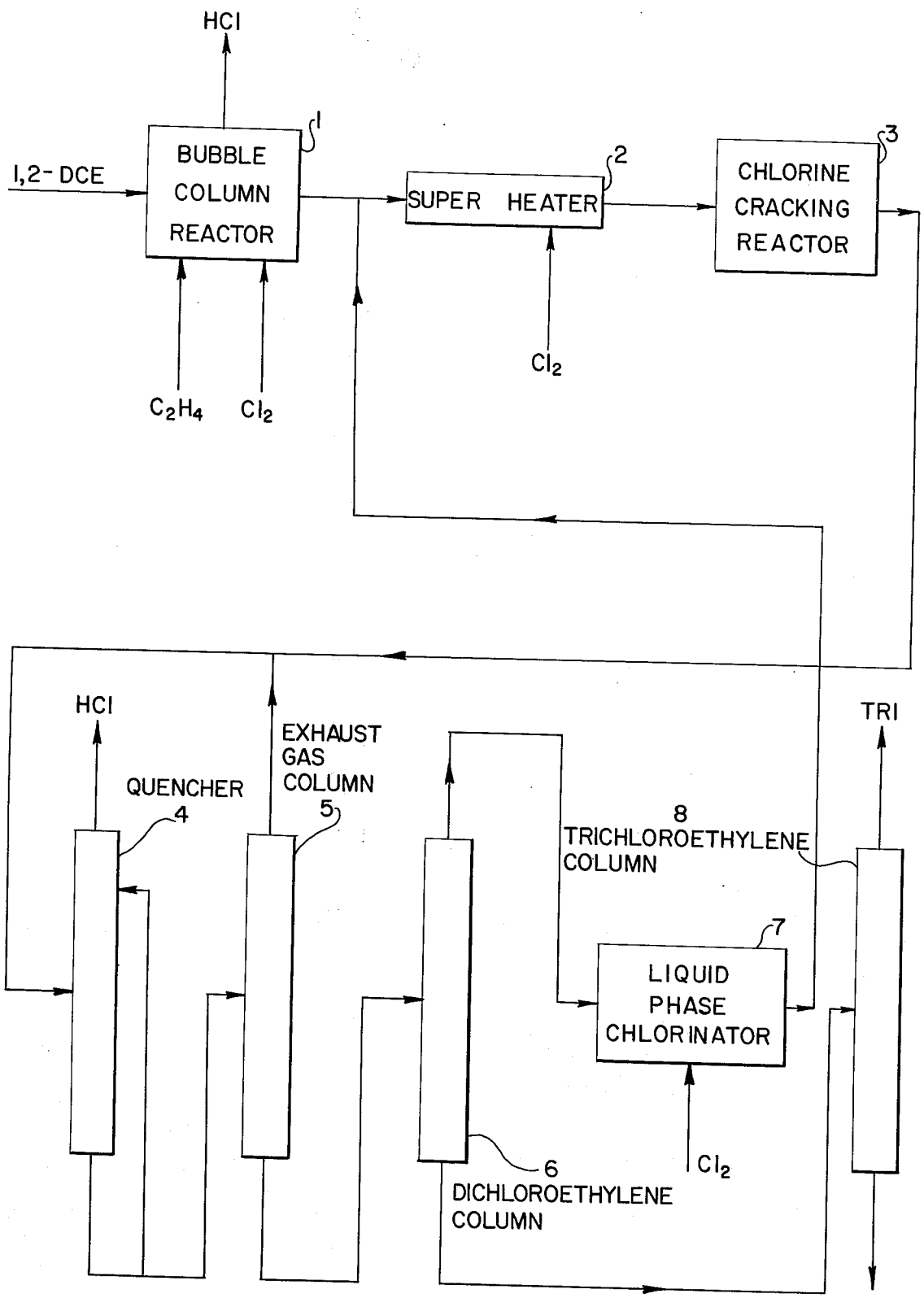

PROCESS FOR PREPARING TRICHLOROETHYLENE

CROSS REFERENCE TO A RELATED APPLICATION

Applicants claim priority under 35 U.S.C. 119 for Application P 23 16 723.9-42, filed Apr. 4, 1973 in the Patent Office of the Federal Republic of Germany.

BACKGROUND OF THE INVENTION

The present invention is concerned with a method for preparing trichloroethylene, starting with 1,2-dichloroethane, wherein the recirculation of incompletely reacted starting materials is considerably reduced.

The state of the art of trichloroethylene production may be ascertained by reference to the Kirk-Othmer "Encyclopedia of Chemical Technology", Second Edition, Vol. 5 (1964), pp. 183–195, under the section TRICHLOROETHYLENE, particularly page 190 where the use of 1,2-dichloroethane as a starting material is mentioned. According to Kirk-Othmer, British Patent Nos. 904,405 and 913,040 disclose that starting with 1,2-dichloroethane, the chlorination may be effected, at 380°–510°C, by a mixture of air and chlorine in the presence of a copper chloride or copper-potassium chloride catalyst. U.S. Pat. No. 3,029,299 of Thermet et al which issued Feb. 3, 1958, discloses that the 1,2-dichloroethane can be converted to trichloroethylene by chlorination in a fluidized bed, at a high flow rate, and at 350°–450°C. According to British Pat. No. 904,084 various $C_1$ to $C_4$ chlorinated and unchlorinated aliphatic-hydrocarbon mixtures are chlorinated to trichloroethylene by chlorine or a hydrogen chloride and oxygen mixture in a fluidized bed, at 290 –500°C, using copper chloride or copper-zinc chloride catalyst.

U.S. Pat. 3,631,207 of Kircher, Jr. et al which issued December 28, 1971, discloses the dehydrochlorination of 1,1,2,2,-tetrachloroethane, 1,1,2,2,-tetrachloroethane, pentachloroethane or mixtures thereof at an elevated temperature of about 145°C to below 300°C in a liquid state while under positive pressure of about 35 p.s.i.a. to 300 p.s.i.a. in the presence of activated carbon to form trichloroethylene, tetrachloroethane or mixtures thereof.

Trichloroethylene is a significant aliphatic chlorinated hydrocarbon. Because of its excellent solubility, it is a preferred means for metal degreasing and is used in chemical cleaning.

It is known to prepare trichloroethylene from acetylene by a variety of processes. However, in view of the high cost of high-energy acetylene, processes have been recently developed, which start from ethane, ethylene or their chlorinated derivatives. One may distinguish between two groups in these recent processes, namely those which lead directly to trichloroethylene at high temperatures and in the gaseous state in purely thermal or also catalytic manner, and those which first chlorinate ethylene in the liquid phase to tetrachloroethane and subsequently convert the latter by means of cracking in the gaseous or liquid phase to trichloroethylene (the 2-stage process). The 2-stage process is generally advantageous with respect to the gaseous process in that there is higher selectivity and simpler removal of the heat of chlorination by partial evaporation of the reagent mixture.

It is known that the substituent chlorination of saturated, organic compounds is much accelerated by the simultaneous presence of chlorine-adding olefins as disclosed in U.S. Pat. No. 1,991,600 of Deanesly, which issued Feb. 19, 1935. Recently this effect has also been applied in various processes for preparing trichloroethylene. For instance, 1,2-dichloroethane is chlorinated in the presence of ethylene to a mixture of chlorinated hydrocarbons containing predominantly tetrachloroethanes, the latter being separated and lending themselves to conversion into trichloroethylene by means of dehydrochlorination.

U.S. Pat. No. 3,631,207 discloses, among other things, a process for preparing trichloroethylene in some cases together with tetrachloroethylene, wherein chlorine and ethylene are reacted in a liquid medium at 0°–250°C, the medium consisting of chloroethanes with at least 2.5 atoms of chlorine per molecule. Subsequently at least part of the chloroethanes are removed, and the product removed is separated into a fraction of higher boiling point containing predominantly chloroethanes with 4 or more chlorine atoms per molecule, and into a lower boiling point fraction of average chlorine content less than that of the first fraction. At least part of the lower boiling-point fraction then is used as the liquid medium for the above-described chlorination reaction, while the higher boiling-point fraction containing predominantly tetra- and pentachloroethanes, is dehydrochlorinated under pressure and in the presence of activated carbon, being in the liquid state and subjected to an elevated temperature of 190°–250°C. Another process (INDUSTRIAL & ENGINEERING CHEMISTRY, Vol. 62, (1970), No. 5, pp. 36–41) in a similar manner chlorinates ethylene in the liquid phase at temperatures from 100° to 130°C and 10 atm. pressure. Subsequently the reaction product is separated into a low boiling-point fraction of dichloroethane and 1,1,2-trichloroethane and into a high boiling-point fraction of tetrachloroethane and pentachloroethane. Again the low boiling-point products are used as the reaction medium for chlorinating ethylene. The tetrachloroethanes and pentachloroethanes are thermally cracked at 450°–500°C under pressure into trichloroethylene and perchloroethylene, with ferric chloride being used in catalytic amounts.

French Pat. No. 1,587,362 discloses how to chlorinate 1,2-dichloroethane in the presence of chlorine derivatives of ethylene, i.e. vinyl chloride, cis-trans-1,2-dichloroethylene and vinylidene chloride (1,1-dichloroethylene), possibly with mixtures therefrom. The catalytic effect of the chlorine derivatives on the substituent chlorination of 1,2-dichloroethylene however is less pronounced than that of ethylene, so that large quantities of 1,2-dichloroethylene must be circulated or cycled, and the space-time yields are appreciably less than when using $C_2H_4$ as a catayst. Following the separation of the 1,2-dichloroethylene from the reaction product, one obtains a mixture of 1,1,2-trichloroethane, tetrachloroethanes and pentachloroethanes, which mixture is dissociated pyrolytically at 450°C, forming vinylidene chloride, cis-trans-1,2-dichloroethylene, trichloroethylene and perchloroethylene. The products are condensed from the hydrogen chloride that was produced simultaneously and the mixture thus obtained is subjected to distillation-separation into a low boiling-point fraction consisting of vinylidene chloride and cis-trans-1,2-dichloroethylene and into a high boiling-point fraction consisting of trichloroethylene and perchloroethylene. The low boiling-point compounds of vinylidene chloride and cis-trans-1,2-dichloroethylene are fed back of chlorinating 1,2-dichloroethane.

However, the above-mentioned and commerically disclosed 2-stage process suffers from the drawback of a relatively high perchloroethylene content in the product and of high expenditures of economical and commercial nature because of the recirculation required for the incompletely reacted feed stock materials: in increasing degree, perchloroethylene is manufactured by means of chlorinating pyrolysis, that is, chlorinating at 600°C with thermal fission or dissociation of the chemical compound, from wastes of chlorinated hydrocarbons. Such a process is becoming increasingly significant in highly industrialized countries because of ecological considerations. Therefore, additional accumulation or output of perchloroethylene is increasingly undesirable and unprofitable.

Now, besides being generated by chlorinating $C_2$ compounds with 4 or fewer chlorine atoms in the molecule in the gaseous phase, perchloroethylene may also be quickly and quantitatively obtained by dehydrochlorinating the pentachloroethane obtained from liquid-phase chlorination of $C_2H_4$ and/or 1,2-dichloroethane. In order to keep the pentachloroethane content low in the liquid-phase chlorination, the latter must proceed with low conversion rates of the reagents, so the recirculation will be high and hence the costs are considerable.

High recirculation rates also occur when dehydrochlorinating pure tetrachloroethanes, because full conversions may not be undertaken if high yields of trichloroethylene and/or avoidance of soot precipitation from the hot walls (an endothermic reaction) are desired. The cycling operation of unreacted feed stock materials cannot take place unless substantial expenditures are met, in the case of preparing trichloroethylene and perchloroethylene, because the boiling points of perchloroethylene and of 1,1,1,2-tetrachloroethane are close to one another, 121°C and 120°–130°C, respectively. Furthermore, the recirculated product must be freed from minute amounts of materials with higher boiling points, predominantly $C_4$ chlorine derivatives, because the latter will enrich the feed and cause interferences. Such separation, too, is expensive, because the boiling points of the recovered initial materials are very high for some components of the mixture (159°C for pentachloroethane).

Essentially the drawbacks discussed above are caused by the attempts in the classical manner, similar to the acetylene process, to obtain symmetrial and/or asymmetrical tetrachloroethane by starting from $C_2H_4$ and/or 1,2-dichloroethane, the tetrachloroethane being cracked in a known pyrolytic manner.

SUMMARY OF THE INVENTION

Having in mind the limitations of the prior art as set forth above, it is an object of the present invention to avoid these limitations.

This object is achieved by a process for the preparation of trichloroethylene by chlorinating 1,2-dichloroethane in the liquid phase in the presence of ethylene followed by pyrolytic chlorination or dehydrochlorination of the reaction product thus obtained, which is characterized by:

a. chlorinating 1,2-dichloroethane in the presence of 1 – 10 mole percent of ethylene based upon chlorine feed in a liquid medium in a bubble column reactor with a chlorine consumption ratio of chlorine/1,2-dichloroethane = (0.7–1.4):1 at a temperature ranging from about 40° to 150°C and with superficial gas velocities exceeding 8 cm/sec. and gas dwell time of about 0.3 to 10 seconds;

b. completely reacting in the gas phase the chlorination product of (a) together with the recirculated tetrachloroethanes from (d) with about 20–70 moles of chlorine to 100 moles of chlorinated hydrocarbons at temperatures from about 380° to 500°C are dwell times from about 20 to 30 seconds;

c. separating the reaction product obtained in stage (b) following removal of the chlorinated hydrocarbons including any vinyl chlorides that may be present, in conventional distillation processes, into a low boiling-point fraction predominantly containing dichloroethylenes and into a high boiling-point fraction predominantly containing trichloroethylene besides a small amount of perchloroethylene and high boiling-point side-products;

d. reacting the low boiling-point fraction from (c) containing the dichloroethylenes in a mixture of symmetrical and asymmetrical tetrachloroethanes with equimolar amounts of chlorine at temperatures from about 60° to 150°C to obtain tetrachloroethanes and by adding the same together with the product from process stage (a) to the process stage (b); and e. separating by distillation the trichloroethylene from the high boiling fraction of (c).

BRIEF DESCRIPTION OF THE DRAWING

The steps of the process of the present invention may best be described by reference to the accompanying drawing depicting a flow sheet.

1,2-Dichloroethane, ethylene and chlorine are reacted in the liquid phase in bubble column reactor 1. The liquid phase chlorinated product is mixed with recirculated tetrachloroethanes from chlorinator 7 and fed into superheater 2 wherein chlorine is added. This mixture is reacted in chlorine cracking reactor 3 and fed to quencher 4. The quenched hydrocarbons are passed to exhaust gas column 5 where the exhaust gas is recirculated to the quencher 4 and the bottoms are fed to dichloroethylene column 6. The low boiling fraction of the dichloroethylene column 6 is passed to chlorinator 7 for further chlorination and recirculation to superheater 2. The high boiling fraction of dichloroethylene column 6 is fed to trichloroethylene column 8 for separation of the trichloroethylene.

DESCRIPTION OF THE PREFERRED EMBODIMENTS

The essential stages of the process of the present invention are described in detail below:

PROCESS STAGE (a)

In this stage, 1,2-dichloroethane is chlorinated in the liquid phase in the presence of ethylene. Success of this reaction is primarily dependant on the ratio of the reacted chlorine to the initial amount of 1,2-dichloroethane or $C_2$-chlorinated hydrocarbons (the chlorine consumption ratio) and on the execution of the reaction. The chlorination in the liquid phase must take place so that a maximum proportion of 1,1,2-trichloroethane is formed in the reaction product.

Starting from 1,2-dichloroethane, a maximum proportion of 1,1,2-trichloroethane is obtained in the reaction product for a chlorine consumption ratio with respect to 1,2-dichloroethane which ranges from 1.0 to 1.2; (In the following, the chlorine consumption ratio denotes the molecular ratio of consumed chlorine to initially present $C_2$ chlorinated hydrocarbons. This magnitude is characteristic in nature, because complete chlorine conversion is always attempted and therefore the chlorine consumption ratio is generally equal to the mole-ratio of initially present chlorine to initially present $C_2$-chlorinated hydrocarbons). As described in greater detail below, a mixture of symmetrical and asymmetrical tetrachloroethanes is added to the $C_2$-chlorinated hydrocarbon mixture prior to the chlorination cracking (stage b), the tetrachloroethanes being formed by chlorine apposition to the dichloroethylenes generated in stage (d). This makes it possible to extend the chlorine consumption ratio over a range from about 0.7 to 1.4 for the chlorination of 1,2-dichloroethane. 1,1,2-Trichloroethane is then the main ingredient of the mixture and the shortcomings listed further below when operating outside this range are not encountered yet: if the chlorine consumption ratio is appreciably less than 0.7, the content of 1,2,-dichloroethane rapidly increases in the reaction mixture. Therefore the ensuing chlorinating cracking (stage b) becomes increasingly exothermal, because twice the number of moles of chlorine are required for converting 1,2-dichloroethane into trichloroethylene than with respect to 1,1,2-trichloroethane. The increasing exothermal heat characteristic of the reaction and the increased chlorine consumption ratio cause larger formation of soot and side-products which can only be avoided at the expense of total conversion. Furthermore, when the chlorine consumption ratio is too low, appreciable quantities of vinyl chloride appear in the reaction product and cause losses because vinyl chloride may be recovered from the exhausting hydrogen chloride gas only with difficulty and against a cost of the purpose of feedback into the chlorination operation.

However, a variation in the process is feasible, if the minor amount of vinyl chloride occurring in the process of the invention already interferes to such extent that a special cleansing or purifying stage is required.

In order to avoid vinyl chloride in the hydrogen chloride, the lesser proportion of 1,2-dichloroethane, which is obtained in view of the selective chlorination of the process of the present invention in contrast to prior art processes (see Table 1), is separated by distillation from the reaction product and fed back. The process that considerably less 1,2-dichloroethane and no 1,1,2-trichloroethane is fed back.

Appreciably exceeding the chlorine consumption ratio of 1.4 in the liquid phase chlorination of 1,2-dichloroethane causes an increase in pentachloroethane in the reaction product that yields perchloroethylene directly during cracking. The latter is as valuable a solvent as trichloroethylene. When the formation of perchloroethylene however is desired in special cases, then a side-yield of it is achieved in this manner at the expense of trichloroethylene output.

In general, no particular purity requirement need be placed on the 1,2-dichloroethane being used, but there should be a content by weight of at least 98 percent of 1,2-dichloroethane, the natural proportion of 1,1,2-trichloroethane causing no interference. There should be less than 20 ppm of oxygen in the chlorine and ethylene, because oxygen inhibits the substituent chlorination.

Execution of the reaction is significant for the practical performance of chlorination, in order to achieve high yields of 1,1,2-trichloroethane with respect to the initial amount of 1,2-dichloroethane. It is surprisingly found that the continuous-stream bubble column which is already used in commercial chlorinations gives evidence of appreciably reduced selectivity for a practically completely mixed product in the liquid phase with respect to 1,1,2-trichloroethane formation when compared to the discontinuous batch reactor. This is shown in Table 1.

However, the previously mentioned drawbacks relating to chlorine cracking occur for lesser selectivity because of the higher contents in 1,2-dichloroethane and pentachloroethane in the feed stock. Even a tube reactor virtually free from any back mixing of the liquid phase and therefore yielding the same spectrum of products as obtained from batch processing, is hardly suitable because it is practically commercially unfeasible for the required amounts of gas of this application. It is found that the problem of the best possible selectivity is solved by using a reactor cascade, by means of which the product spectrum depending on the number of reactors is adapted in desired manner to the product spectrum of batch operation, the reactor cascade thereby being considered a preferred embodiment of the process of the present invention. It is shown in Table 1 that an appreciable increase in selectivity of the intermediate products is achieved when a cascade of 3 bubble column reactors is used and that 7 reactors series produce the same results as batch operation, advantages are still retained with respect to the present

TABLE 1

| Nature of reaction | Product spectra from chlorinating 1,2-dichloroethane with various reaction procedures | | | | | | | |
|---|---|---|---|---|---|---|---|---|
| | Chlorine consumption ratio * | Pressure (atm.) | Temp. °C | PRODUCT SPECTRUM (Mol. - %) | | | | |
| | | | | 1,2 | 1,1,2 | 1,1,1,2 | 1,1,2,2 | 5 | 6 |
| Batch operation (discontin.) | 1:1.16 | 3 | 124 | 14.9 | 65.8 | 8.7 | 9.5 | 1.1 | — |
| Continuous bubble column reactor (strong feedback) | 1:1.14 | 3 | 122 | 27.8 | 47.7 | 10.3 | 10.6 | 3.5 | 0.1 |
| 3-column cascade | 1:1.10 | 3 | 122 | 20.9 | 56.5 | 10.0 | 10.7 | 1.9 | — |
| 7-column reactor cascade | 1:1.04 | 3 | 110 | 17.3 | 65.2 | 8.0 | 8.6 | 0.9 | — |

* ratio of chlorinated hydrocarbons to $Cl_2$; the reacted ethylene is added to the chlorinated hydrocarbons.

The conversion of chlorine in the process of the present invention essentially depends on the dwell time and magnitude of the "gas-liquid" phase boundary area. The influence of temperature of reaction is fairly and comparatively minor in the temperature range being claimed. Large exchange areas are warranted if superficial gas velocities exceed 8 cm/sec. In this range, the magnitude of the exchange area varies only slightly for increasing gas loading. The exchange area decreases even more below a superficial gas velocity of 8 cm/sec., hence the related reaction speed drops markedly to a point that the process no longer seems commercially feasible. In order to obtain favorable space-time yields, one should therefore select superficial gas velocities of as high a value as possible, of which the upper limit however is determined by the liquid discharge rates. The superficial gas velocity is somewhat lower for tubes of larger diameters (exceeding 50 cm) than for tubes of smaller diameters, wherein higher speeds are possible on account of higher frictional losses. Nevertheless, tubes of smaller diameter present a greater danger of gas-bubble formation, particularly when the diameters of such bubbles are equal to the diameter of the tube (piston bubbles), so that discharge is again favored. The specific examples of the present invention show that liquid discharge begins for superficial gas velocities approximately in the range of 70 cm/sec.

Temperatures between about 40° and 150°C are selected for liquid phase chlorination of 1,2-dichloroethane. In principle, one may also operate outside this range, but when the temperature is considerably below 40°C, the substitution reaction rates become slight and heat transfer difficult, because when the temperature drops below the boiling point of the mixture (atmospheric boiling point of 1,2-dichloroethane: 84°C), it is difficult to make use of evaporation cooling, which is quite convenient otherwise. Above 150°C, there is noticeable dechlorination of the chlorine hydrocarbons.

Reaction pressures of from about 3 to 10 atmospheres are found favorable for obtaining high space-time yields.

The dwell times required for obtaining complete chlorine conversion for the reaction conditions stated fall between about 0.3 and 10 seconds, predominantly between 2 and 3 seconds. Complete chlorine conversion for dwell times less than 0.3 seconds are only obtained in an expensive manner (for instance by adding large exchange surfaces). Dwell times exceeding 10 seconds for the empirical procedures of the process of the present invention are required in no case and entail unnecessarily large reactors.

It is further found that ethylene conversion and the rate of chlorine consumption hardly depend on the ethylene concentration in the process of the invention. It is therefore appropriate to work generally with the least possible amount of ethylene, because it adds chlorine in the form of dichloroethane formation, so that the content of dichloroethane increases in the liquid product mixture, resulting in the limitations already described. It is shown that these limitations are particularly apparent when more than 10 mole percent of ethylene with respect to the feed chlorine is used to react with 1,2-dichloroethane. The process of the present invention therefore should exclude quantities of ethylene appreciably in excess of 10 mole percent with respect to the initial amount of chlorine. If less than 1 mole percent is used, the reaction "extinguishes", or else, it is not initiated at all. The preferred range of concentration of ethylene for chlorinating in the liquid phase therefore is from 1–5 mole percent with respect to the input chlorine. There is a further advantage in small amounts of ethylene in that the ethylene content of the hydrogen chloride being formed (exhaust gas) is kept very low.

One also considers the nature of the material while carrying out the chlorinating reaction. It is known that traces of $FeCl_3$ so strongly catalyze the addition of chlorine to double bonds that the accelerating chlorine substitution effect of ethylene is largely suppressed. Materials containing iron or metals from the iron group, such as cobalt or nickel, therefore are unsuitable in the reaction zones of the substituent chlorination with ethylene. Leaded apparatus is used advantageously.

PROCESS STAGE (b)

As regards the ensuing direct pyrolytic treatment of the chlorine-hydrocarbon mixture obtained following liquid phase chlorination and predominantly consisting of 1,1,2-trichloroethane, 1,2-dichloroethane and 1,1,1,2- as well as 1,1,2,2-tetrachloroethane, pyrolytic chlorination and cracking are performed in parallel and this stage is denoted as "chlorination cracking". The known catalytic effect of chlorine on the pyrolytic cracking of chlorinated hydrocarbons is put to use in this instance. It is surprisingly found that under suitable conditions, 1,2-dichloroethane and 1,1,2-trichloroethane are attacked in preferred manner by chlorine, while the simultaneously present tetrachloroethanes are predominantly dissociated into trichloroethylene but not chlorinated into pentachloroethane, or chlorinated with HCl dissociation of same into perchloroethylene. In conformity with the present invention, the mixture of chlorinated hydrocarbons reaching the chlorinating cracking stage in conformity with stages (a) and (c) is characterized by the following concentration ranges:

| | |
|---|---|
| 1,2-dichloroethane | 2 – 26 mole percent |
| 1,1,2-trichloroethane | 40 – 53 mole percent |
| 1,1,1,2-tetrachloroethane | 5 – 17 mole percent |
| 1,1,2,2-tetrachloroethane | 25 – 33 mole percent |
| pentachloroethane | 0.1 – 2 mole percent |

Chlorination preferably takes place with a chlorine consumption molar ratio of chlorine to chlorinated hydrocarbons = 0.20 to 0.70, preferably from 0.40 to 0.60, at temperatures from about 380° to 500°C, preferably from about 420° to 450°C. A chlorine ratio outside the above stated limits may be used, but such an action only entails limitations of the initial object of the invention. Use of a chlorine consumption ratio, i.e. chlorine/chlorinated hydrocarbons, exceeding 0.7 increases the output of undesired perchloroethylene and of highly chlorinated substances. A chlorine consumption ratio, i.e. chlorine/chlorinated hydrocarbons less than 0.20 produces a higher proportion of chlorinated ethylenes, namely vinyl chloride, vinylidene chloride and cis-trans-1,2-dichloroethylene, of which the separation, recovery and feedback via a chlorination stage causes higher expenditures in time and money. The preferred temperature range of about 420° to 450°C for chlorination cracking requires dwell times of about 20 – 30 seconds for complete chlorine conversion. Deviations from these process limitations at higher temperatures and shorter dwell times bring about higher proportions of interfering, highly chlorinated side products, together with increased danger of soot formation, whereas long dwell times, that is very low space-time yields from the reactor, are required for low temperatures.

An essential advantage inherent in this kind of execution of the chlorination reaction in the gas phase is the lack of calorific effects of the reaction, because the combination of the exothermal chlorination with the endothermic dehydrochlorination reaction in the ratio of the concentrations of the materials necessarily determined by the invention prevent the occurrence of appreciable heat effects. Thereby very precise tolerance is permitted with respect to the required temperature range and hence the reactions take place very selectively, so that the output of undesired side-products are a minimum for the conditions set down by the invention.

A preferred execution of the process stage (b) consists in a tube reactor heated by means of a heat carrier to the optimal process temperature in the reaction tubes. In view of the required high temperatures from about 420° to 450°C, suitable heat carriers are salt melts, for instance melts of KNO$_3$, NaNO$_3$, NaNO$_2$.

The question of the materials of the reactor tubes is of appreciable significance for the process of the present invention, where the chlorination cracking takes place. Preferred materials are nickel-chromium alloys, for instance INCONEL (registered trademark), whereas iron alloys, for instance V4A steel, even when resistant to the stringent conditions of the requirements, is less appropriate because it causes higher concentrations in perchloroethylene and highly chlorinated substances.

Pyrolytic chlorination is advantageously undertaken without a catalyst in empty tubes. Clearly, it is feasible to make use of conventional chlorination catalyst such as activated carbon or adsorbing materials that were reacted with metal salts, but executing the process in this manner lacks appreciable advantages because of the costs induced by a catalyst, because its life is limited and because it insignificantly only reduces the formation of side-products, if it does not raise them. When the process of the present invention is executed in the above-described manner, one obtains a mixture of substances with components of the following concentrations:

| | |
|---|---|
| vinyl chloride | 1.1 mole percent |
| vinylidene chloride | 3.4 mole percent |
| 1,2-dichloroethylene (cis + trans) | 26.8 mole percent |
| trichloroethylene | 62.3 mole percent |
| carbon tetrachloride | 0.06 mole percent |
| 1,2-dichloroethane | 0.02 mole percent |
| 1,1,2-trichloroethane | 0.1 mole percent |
| perchloroethylene | 4.1 mole percent |
| 1,1,1,2-tetrachloroethane | 0.2 mole percent |
| 1,1,2,2-tetrachloroethane | 0.3 mole percent |
| pentachloroethane | 0.8 mole percent |
| highly chlorinated substances (MW250) | 0.8 mole percent |

This mixture of chlorinated hydrocarbons is processed in the next process stage.

PROCESS STAGES (c) and (d)

These process stages comprise the final processing of the gaseous crude product from chlorination cracking and the chlorination of the dichloroethylenes into tetrachloroethanes, which, together with the product from the liquid phase chlorination of 1,2-dichloroethane is chlorination-cracked. First the hot reaction gases are quenched, then the residual dissolved hydrogen chloride together with minute amounts of vinyl chloride are driven out through an exhaust gas column and the raw product is separated into two fractions by means of distillation. The first fraction (I) contains the low-boiling point components vinylidene chloride and 1,2-dichloroethylene (cis + trans), the second fraction (II) contains trichloroethylene and higher boiling-point side reaction products. Fraction (II) is recitified in order to obtain pure trichloroethylene. Fraction (I) is chlorinated in the liquid phase by addition of stoichiometric amounts of chlorine to form 1,1,1,2-and 1,1,2,2-tetrachloroethane. The chlorination takes place without addition of catalytically acting iron salts, i.e., thereby avoiding ferrous materials, because separating dissolved iron salts from the product involves additional cost expenditures, or if not removed, adversely affect the subsequent chlorination cracking. It is found that dichloroethylenes dissolved in tetrachloroethanes selectively add chlorine (so-called "induced chlorination") at temperatures ranging from 60° to 150°C and at pressures (automatically) setting in above the mixtures (boiling points: vinylidene chloride = 32°C; dichloroethylenes = 46°C (trans); 60°C (cis)), while no appreciable reaction of the already present tetrachloroethanes is observed with chlorine, the latter appearing only above 150°C. The chlorination product from stage (d) consists virtually of tetrachloroethanes and need not be freed from any dissolved chlorine still present. This chlorination product may be directly combined with the chlorination product of the 1,2-dichloroethane from stage (a) and be chlorine cracked in stage (b).

The pressure applied for executing the entire process are determined by the boiling-points of the substances and mixtures and by the space-time yields of the reactors. The low boiling-point of several chlorinated hydrocarbons requires cooling facilities in the presence of unduly low pressures in order to condense the largest part of these chlorinated hydrocarbons from the exhausting, gaseous sideproducts. Ordinary water cooling suffices at higher pressures. Furthermore, the reaction rates are appreciably increased by raising the pressure in the liquid phase chlorination of 1,2-dichloroethane, whereby higher space-time yields are obtained. A preferred pressure range lies from about 2 to 10 atmospheres, the limits being set on appreciably higher pressures by the required evaporation temperatures of the liquid products.

One may view the advantages obtainable from the present process from the fact that trichloroethylene is generated from 1,2-dichloroethane with high selectivity by precisely adjusting the two steps in the process, chlorination in the liquid phase and direct chlorine cracking of the product in the gas phase. This manner of executing the reaction allows a virtually complete conversion of the initial substances and therefore terminal processing of the reaction mixture in order to feed back non-converted initial products is no longer economically profitable.

The following examples are set forth as illustrative of the process of the present invention. They are intended to serve merely as examples thereof since many other conditions of operation would come within the scope of the present invention.

EXAMPLE 1

The process of the present invention is carried out in a semi-industrial testing facility shown schematically in the FIGURE. Processing continues over an appreciable time. Unless otherwise noted, all tubes and equipment consist of glass.

The facility consists of a bubble column reactor 1, i.e., an internally lead coated iron pipe 260 cm long and 80 mm ID, provided with a heating or cooling jacket and with a heat exchanger circulation system. About 15 liters of liquid are contained in the reaction system, the content of the reactor proper (without circulation system) being about 10 liters. 1,2-Dichloroethane (1,2-DCA) is metered into the circulation system and the chlorination product is removed at the top of the bubble column proper. Chlorine ($Cl_2$) and ethylene ($C_2H_4$) are introduced at the lower end of the reactor by means of distributing inputs, the ethylene inlet being located about 10 cm above that for the chlorine. The exhaust gas (hydrogen chloride and non-converted ethylene) is withdrawn by means of three cooling units operating with cooling brine ($-18°C$), these cooling units cooling down to about $+15°C$. A control valve is placed after the cooling units, keeping the system at a constant pressure of 3 atmospheres.

Part of the exhaust gas is made to pass over a wash tower loaded with 12 percent by weight caustic soda solution in order to determine ethylene conversion. The residual gas, following prior deep cooling for condensing water and chlorinated hydrocarbons still present is measured by means of the gas meter.

The chlorination product generated in reactor 1 passes to a vessel in which it is mixed with the reaction product from chlorinator 7. The combined product streams are then evaporated at temperatures from about 150° to 170° C in the evaporator and are mixed with the measured, pre-heated quantity of chlorine in a superheater 2 where the temperature is raised to 250° C. The evaporator and superheater 2 are made of Inconel and the fillers in the mixing chamber are quartz.

The reaction gas then enters reactor 3, wherein chlorine cracking takes place in the manner already described in detail. Again the system is kept at 3 atmospheres by means of a pressure regulating valve after reactor 3.

Reactor 3 consists of 10 empty inconel pipes 250 cm long and 80 mm in ID, which are heated by a eutectic salt $KNO_3$—$NaNO_3$—$NaNO_2$. Such reactors are already successfully used in oxidations (for instance phthalic acid anhydride from naphthalene) and belong to the state of the art.

The hot gas stream leaving the reactor 3 is cooled in the quencher 4 and most of the hydrogen chloride (HCl) is separated therein. The residual HCl is removed in a subsequent exhaust gas column 5. In column 6 the dichloroethylenes are removed at the top in order to convert them in the chlorinator 7 by "induced chlorination", that is, without a catalyst, into the corresponding tetrachloroethanes. Chlorinator 7 proper consists of an enameled agitated vessel of 50 liter capacity, the contents of which are pumped around in order to get rid of the reaction heat by means of an external cooler. The dichloroethylenes and an equivalent amount of chlorine are continuously supplied to this section of the circulatory system via inlet tubes. The reaction product is removed at the upper part of the agitated vessel and combined with the product from 1.

The agitated vessel is filled with the product tetrachloroethanes. The reaction temperature is 100°C, the pressure is 3 atmospheres and the liquid dwell time is about 2 hours. It is found that the tetrachloroethanes used as solvents and generated during the reaction are attacked by chlorine only when the dichloroethylenes are reacted virtually completely. The product resulting from the described procedure in chlorinator 7 has the following composition.

| | |
|---|---|
| symmetrical dichloroethylene: | 0.8 mole % = 0.5 % by weight |
| 1,1,2,2-tetrachloroethane: | 86.5 mole % = 85.7 % by weight |
| 1,1,1,2-tetrachloroethane: | 8.7 mole % = 8.6 % by weight |
| pentachloroethane: | 2.0 mole % = 2.4 % by weight |
| hexachloroethane: | 2.0 mole % = 2.8 % by weight |

Lastly, from the sump product of the dichloroethylene column 6, pure trichloroethylene is obtained by rectification in the trichloroethylene column 8.

The described facility was operated for some time under the following conditions: 430 moles/hour (42.6 kg/hour) of 1,2-dichloroethane; 500 moles/hour of chlorine and 50 moles/hour of ethylene were reacted at a temperature of 122° C and a pressure of 3 atmospheres in bubble column reactor 1.

The specifications of the materials used are as follows:

| | |
|---|---|
| 1,2-dichloroethane: | 99.9% by weight (0.1% by weight of 1,1,2-trichloroethane) |
| chlorine | 99.94% by volume (0.035% by volume of $CO_2$; 0.002 % by volume of $H_2$; 0.001 % by volume of $O_2$; 0.019 % by volume of $N_2$; 0.0001% by volume of CO) |
| ethylene | 99.99% by volume (0.01 % by volume of inerts) |

Chlorination provided the following product spectrum:

| | |
|---|---|
| 1,2-dichloroethane | 28.4 mole % = 21.0% by weight |
| 1,1,2-trichloroethane | 46.3 mole % = 46.2 % by weight |
| 1,1,1,2-tetrachloroethan | 10.4 mole % = 13.1 % by weight |
| 1,1,2,2-tetrachloroethane | 11.0 mole % = 13.8 % by weight |
| pentachloroethane | 3.8 mole % = 5.7 % by weight |
| hexachloroethane | 0.1 mole % = 0.2 % by weight |

The superficial gas velocity is 31 cm/sec and the gas dwell time is about 2 sec.

67.4% of the input ethylene is reacted with chlorine. The molecular ratio of chlorine to the input $C_2$ compounds (1,2-dichloroethane + ethylene) is, ($Cl_2$)/(chlorinated hydrocarbon) = 1.04.

The total rate of $C_2$ material being given off is 464 moles/hour.

Taking into account the feedback of the tetrachloroethanes obtained in the stationary operating condition in stage (d), the following mixture is obtained for the input to the chlorine cracking reactor 3:

| | |
|---|---|
| 1,2-dichloroethane | 22.5 mole % = 15.8 % by weight |
| 1,1,2-trichloroethane | 36.7 mole % = 34.7% by weight |
| 1,1,1,2-tetrachloroethane | 10.3 mole % = 12.3% by weight |
| 1,1,2,2-tetrachloroethane | 27.4 mole % = 32.7 % by weight |
| pentachloroethane | 3.0 mole % = 4.3 % by weight |
| hexachloroethane | 0.1 mole % = 0.2% by weight |

The reactions for chlorine cracking in stationary operation are carried out under the following conditions:

| | |
|---|---|
| maximum temperature | 436°C |
| pressure in reactor | 3 atmospheres |
| gas dwell time | about 24 sec. |
| molar input ratio, chlorine to chlorinated hydrocarbons | 0.57 |
| chlorine conversion | 100% |
| $C_2$ hydrocarbon input | 625 moles/hour (of which 161 moles/hour feedback is tetrachloroethanes) |
| chlorine input | 356 moles/hour |

The reaction product from the chlorine cracking was of following composition:

| | |
|---|---|
| vinyl chloride | 2.3 mole % = 1.2% by weight |
| vinylidene chloride | 2.4 mole % = 1.9 % by weight |
| symmetrical dichloroethylene | 23.4 mole % = 18.2 % by weight |
| carbon tetrachloride | 0.08 mole % = 0.10% by weight |
| 1,2-dichloroethane | 0.04 mole % = 0.03 % by weight |
| trichloroethylene | 63.3 mole % = 66.7% by weight |
| perchloroethylene | 6.1 mole % = 8.1 % by weight |
| 1,1,2-trichloroethane | 0.1 mole % = 0.1% by weight |
| 1,1,1,2-tetrachloroethane | 0.2 mole % = 0.3 % by weight |
| 1,1,2,2-tetrachloroethane | 0.5 mole % = 0.7% by weight |
| pentachloroethane | 1.0 mole % = 1.6% by weight |
| high boiling point substances (MWca 250) | 0.6 mole % = 1.1% by weight |

Trichloroethylene is obtained from this mixture with a purity of 99.9% by weight by rectification (contaminations: 0.06% by weight of carbon tetrachloride and 0.04% by weight of 1,2-dichloroethane).

Hence the yield in trichloroethylene amounts to 92 mole percent with respect to the input of 1,2-dichloroethane and 85 mole percent with respect to the input of 1,2-dichloroethane including the converted ethylene.

EXAMPLE 2

All other equipment of the apparatus of Example 1 remaining the same, the bubble column reactor 1 is replaced by a cascade of seven bubble column reactors. Each individual one consisted of a glass tube with double walls for the purposes of conductivity, 110 cm in length and 40 mm in ID, provided at the lower end with a lateral inlet for the liquid reaction product from the preceding reactor and for the supply of ethylene and chlorine. Chlorine is supplied centrally from below, while ethylene is supplied laterally 100 mm above. An opening is located at the upper end of the reaction tube for the overflow of the reaction product into the next reactor. Every reactor is equipped with an exhaust gas cooling unit comprising cooling brine (−18° C) and is interconnected by a collecting line for the hydrogen chloride generated, being kept at constant pressure by a regulating valve mounted in this line.

Operation of the apparatus thus modified takes place under the following conditions: 351 moles/hour (34.8 kg/hour) of 1,2-dichloroethane, 394 moles/hour of chlorine and 28 moles/hour of ethylene are reacted at temperatures of from about 110 to 130° C and 3 atmospheres pressure in the above-described cascade of seven bubble column reactors (specification of input substances: same as in Example 1).

1,2-Dichloroethane is continuously fed to the first reactor; the chlorination product being withdrawn from the top of the last one.

Approximately 1/7 of the total input of chlorine and ethylene amounts is fed to each reactor. The reaction temperatures in the reactors rises with increasing degree of chlorination from 110° C to roughly 130° C.

For chlorine conversion of 100% and ethylene conversion of 70.2%, the following product composition is achieved:

| | |
|---|---|
| 1,2-dichloroethane | 17.3 mole % = 12.8% by weight |
| 1,1,2-trichloroethane | 65.2 mole % = 65.0 % by weight |
| 1,1,1,2-tetrachloroethane | 8.0 mole % = 10.0% by weight |
| 1,1,2,2-tetrachloroethane | 8.6 mole % = 10.8% by weight |
| pentachloroethane | 0.9 mole % = 1.4 % by weight |

The superficial gas velocity for each reactor is about 13 cm/sec. and the gas dwell time is about 2 seconds. The reaction product (at a total rate of 371 moles/hour) is subsequently combined with the tetrachloroethanes obtained from the chlorination of the dichloroethylenes, and subjected to chlorine cracking as explained in Example 1. The evaporation temperature of the mixture chlorine-hydrocarbons is about 150°–170° C, the reaction temperature is about 425° C. The pressure in the reactor is 3 atmospheres and the gas dwell time is about 29 seconds. The subsequent chlorination of the dichloroethylenes is performed as in Example 1.

Upon reaching the stable state, the following data are obtained for chlorine cracking:

Input mixture, taking into account feedback tetrachloroethanes:

| | |
|---|---|
| 1,2-dichloroethane | 13.4 mole % = 9.4% by weight |
| 1,1,2-trichloroethane | 49.9 mole % = 47.0% by weight |
| 1,1,1,2-tetrachloroethane | 9.2 mole % = 10.9% by weight |
| 1,1,2,2-tetrachloroethane | 26.9 mole % = 31.9 % by weight |
| pentachloroethane | 0.6 mole % = 0.8 % by weight |

The molar input ratio of chlorine to chlorinated hydrocarbons = 0.49 and the total input for chlorine cracking:

$C_2$ compounds: 530 moles/hour (of which 160 moles/hour are feedback tetrachloroethanes)

chlorine: 260 moles/hour
chlorine conversion: 100%
Product mixture obtained following chlorine cracking:

| | |
|---|---|
| vinyl chloride | 1.1 mole % = 0.5% by weight |
| vinylidene chloride | 3.4 mole % = 2.7 % by weight |
| symmetric dichloroethylene | 26.8 mole % = 21.1% by weight |
| carbon tetrachloride | 0.06 mole % = 0.08 % by weight |
| 1,2-dichloroethane | 0.02 mole % = 0.02 % by weight |
| trichloroethylene | 62.3 mole % = 66.3% by weight |
| perchloroethylene | 4.1 mole % = 5.5 % by weight |
| 1,1,2-trichloroethane | 0.1 mole % = 0.1% by weight |
| 1,1,1,2-tetrachloroethane | 0.2 mole % = 0.3% by weight |
| 1,1,2,2-tetrachloroethane | 0.3 mole % = 0.4% by weight |
| pentachloroethane | 0.8 mole % = 1.3% by weight |
| high boiling point substances (mol wt. = about 250) | 0.8 mole % = 1.7% by weight |

Thus the yield in trichloroethylene amounted to 94 mole % with respect to 1,2-dichloroethane input and 89 mole % with respect to the input of 1,2-dichloroethane including converted ethylene.

EXAMPLE 3.

The following example shows the conditions attending feedback of 1,2-dichloroethane following liquid phase chlorination, whereby there is no vinyl chloride in the hydrogen chloride after chlorine cracking. The equipment and the process of Example 2 are used. Corresponding to the data listed therein for product composition and product stream following liquid phase chlorination of 1,2-dichloroethane, 64 moles/hour of 1,2-dichloroethane are separated by distillation in an additional column from the chlorinated hydrocarbon mixture, so that the product mixture listed below is obtained from the first stage (total rate: 307 moles/hour):

| | |
|---|---|
| 1,1,2-trichloroethane | 78.8 mole % = 74.5 % by weight |
| 1,1,1,2-tetrachloroethane | 9.7 mole % = 11.5% by weight |
| 1,1,2,2-tetrachloroethane | 10.4 mole % = 12.4% by weight |
| pentachloroethane | 1.1 mole % = 1.6% by weight |

This product mixture is subsequently combined with the tetrachloroethanes obtained from chlorinating the dischloroethylenes and are then subjected to the chlorine cracking of Example 1. The following stable operational state is obtained from chlorine cracking:

Input mixture, taking into account feedback tetrachloroethanes:

| | |
|---|---|
| 1,1,2-trichloroethane | 59.5 mole % = 53.8% by weight |
| 1,1,1,2-tetrachloroethane | 12.0 mole % = 13.6 % by weight |
| 1,1,2,2-tetrachloroethane | 27.7 mole % = 31.5% by weight |
| pentachloroethane | 0.8 mole % = 1.1 % by weight |

Molar input ratio of chlorine to chlorinated hydrocarbons: 0.32
Total input for chlorine cracking:
C$_2$ compounds = 450 moles/hour (of which 143 moles/hour are feedback tetrachloroethanes)
chlorine = 144 moles/hour
chlorine conversion = 100%
Product mixture obtained following chlorine cracking:

| | |
|---|---|
| vinylidene chloride | 5.3 mole % = 4.2% by weight |
| symmetrical dichloroethylene | 26.4 mole % = 20.8 % by weight |
| carbon tetrachloride | 0.1 mole % = 0.1% by weight |
| trichloroethylene | 62.6 mole % = 66.9 % by weight |
| perchloroethylene | 3.3 mole % = 4.4 % by weight |
| 1,1,2-trichloroethane | 0.2 mole % = 0.2% by weight |
| 1,1,1,2-tetrachloroethane | 0.4 mole % = 0.6% by weight |
| 1,1,2,2-tetrachloroethane | 0.6 mole % = 0.8 % by weight |
| pentachloroethane | 0.5 mole % = 0.8 % by weight |
| high boiling point substances | (MW about 250) |

The yield in trichloroethylene with respect to input 1,2-dichloroethane taking into account the feedback 1,2-dichloroethane therefore amounts to 97 mole %, and 92 mole % when the converted ethylene is included.

We claim:

1. In a process for making trichloroethylene by chlorinating 1,2-dichloroethane in the liquid phase in the presence of ethylene followed by simultaneous chlorination and dehydrochlorination of the liquid phase reaction product, the improvement comprising:
   a. chlorinating 1,2-dichloroethane in the liquid phase in the presence of about 1 to 10 moles percent of ethylene relative to chlorine employed with a chlorine feed molar consumption ratio of chlorine to 1,2-dichloroethane of about 0.7 to 1.4 to 1 at temperatures ranging from about 40° to 150° C, a superficial gas velocity in excess of 8 cm/second and gas dwell times of about 0.3 to 10 seconds producing a liquid phase chlorinated product;
   b. reacting said liquid phase chlorinated product in the gas phase with recycled tetrachloroethanes and chlorine wherein about 20 – 70 moles of chlorine are reacted with 100 moles of chlorinated hydrocarbons at temperatures of from about 380° to 500° C and the dwell times are about 20 to 30 seconds producing a gas phase chlorinated product;
   c. said gas phase chlorinated product is quenched to separate hydrogen chloride and producing a quenched gas phase chlorinated product, said quenched gas phase chlorinated product is separated by distillation into a low boiling point dichloroethylene fraction and a high boiling point trichloroethylene fraction;
   d. reacting said dichloroethylene fraction in the liquid phase with equimolar amounts of chlorine at temperatures of from about 60° to 150° C to produce said recycled tetrachloroethanes comprising symmetrical and asymmetrical tetrachloroethanes and recycling said tetrachloroethanes to step (b); and
   e. separating by distillation said high boiling point trichloroethylene fraction to produce trichloroethylene product.

2. The process of claim 1, wherein said liquid phase chlorinating of step (a) takes place in a bubble column reactor.

3. The process of claim 2, having 3 to 10 of said bubble column reactors in cascade and said chlorine feed consumption ratio of chlorinated hydrocarbons to chlorine of step (a) is about 1 to 1.0 – 1.2.

4. The process of claim 3, having seven bubble column reactors in cascade.

5. The process of claim 1, wherein said liquid phase chlorinating of step (a) is carried out at temperatures of about 100° – 130° C.

6. The process of claim 1, wherein said gas phase reaction of step (b) is carried out in empty reaction tubes in a temperature range of from about 420° to 450° C and for a ratio of about 40 – 60 moles of chlorine to 100 moles of chlorinated hydrocarbons.

7. The process of claim 1, wherein said chlorination of step (d) is carried out at temperatures of about 80° – 105° C.

8. The process of claim 1, wherein the reactions of steps (a), (b) and (d) are carried out under pressures of about 1 – 20 atmospheres.

9. The process of claim 8, wherein said pressure range is 3 – 10 atmospheres.

10. The process of claim 1, wherein ethylene is added in amounts of about 1 – 5 mole percent referred to the amount of feed chlorine in step (a).

11. The process of claim 1, wherein unconverted 1,2-dichloroethane is separated from the chlorinated product of step (a) and is recycled to step (a) and the remaining mixture of chlorinated hydrocarbons free from 1,2-dichloroethane supplied to step (b) and hydrogen chloride free from vinyl chloride is withdrawn from step (b).

* * * * *